United States Patent [19]

Reimold et al.

[11] Patent Number: 5,584,879
[45] Date of Patent: Dec. 17, 1996

[54] AORTIC VALVE SUPPORTING DEVICE

[75] Inventors: Sharon C. Reimold, Boston; Richard T. Lee, Weston; Scott D. Solomon, Boston, all of Mass.

[73] Assignee: Brigham & Women's Hospital, Boston, Mass.

[21] Appl. No.: 507,919

[22] Filed: Jul. 27, 1995

Related U.S. Application Data

[63] Continuation of Ser. No. 166,446, Dec. 13, 1993, abandoned.

[51] Int. Cl.[6] .................................................. A61F 2/24
[52] U.S. Cl. ............................ 623/2; 606/157; 606/158
[58] Field of Search ........................ 623/2, 900; 606/151, 606/153, 157, 158, 29; 600/29; 128/DIG. 25

[56] References Cited

U.S. PATENT DOCUMENTS

| | | | |
|---|---|---|---|
| 3,001,546 | 10/1958 | Salisbury | 623/2 |
| 3,726,279 | 4/1973 | Barefoot et al. | |
| 4,211,325 | 4/1980 | Wright | 623/2 |
| 4,401,107 | 8/1983 | Haber et al. | 128/DIG. 25 |
| 4,551,862 | 11/1985 | Haber | 623/14 |
| 4,576,605 | 3/1986 | Kaidash et al. | 623/2 |
| 4,693,236 | 9/1987 | Leprevost | 128/DIG. 25 |
| 4,725,274 | 2/1988 | Lane et al. | 623/2 |
| 4,759,758 | 7/1988 | Gabbay . | |
| 5,071,431 | 12/1991 | Sauter et al. | 623/2 |
| 5,131,905 | 7/1992 | Grooters . | |
| 5,163,955 | 11/1992 | Love et al. | 623/2 |
| 5,234,447 | 8/1993 | Kaster et al. | 606/153 |
| 5,352,183 | 10/1994 | Jonsson et al. | 600/32 |

FOREIGN PATENT DOCUMENTS

| | | |
|---|---|---|
| 2688692 | 3/1992 | France . |
| 2254254 | 3/1992 | United Kingdom . |

*Primary Examiner*—Michael J. Milano
*Attorney, Agent, or Firm*—Hamilton, Brook, Smith & Reynolds, P.C.

[57] ABSTRACT

An aortic valve supporting device having an annular portion located around a central axis with stenting arms extending axially from the annular portion. A hiatus is formed in the annular portion to permit the annular portion and the stenting arms to be positioned around the aorta with the stenting arms in position to apply a supporting force to the aortic valve.

19 Claims, 3 Drawing Sheets

AORTIC VALVE SUPPORTING DEVICE

RELATED APPLICATION

This application is a continuation of application Ser. No. 08/166,446 filed on Dec. 13, 1993, which is incorporated herein by reference in its entirety.

BACKGROUND OF THE INVENTION

The heart is basically a hollow, muscular, organ which is, in effect, a pump. It is divided into four chambers, the left and right ventricle, and the left and right atrium. The main pumping chamber of the heart is the left ventricle. It pumps blood through the aortic valve in the aorta to the various arteries and hence, to the rest of the body. The aortic valve is a one-way valve which permits blood to flow from the left ventricle but when functioning properly, closes to prevent blood from flowing in the opposite direction, i.e. back to the left ventricle.

The aortic valve comprises three leaflets or cusps, which during systole, i.e. the time the heart is contracting, open to permit the outward flow. During diastole, i.e. when the heart is relaxed, the aortic valve normally closes to prevent the reverse flow of blood, i.e. regurgitation from the aorta into the left ventricle. Patients which experience aortic regurgitation have, for any number of reasons, incompetence or partial malfunction of the aortic valve. As a result, during diastole, when the heart is itself in its most relaxed condition and the interior pressure is at the lowest, blood from the then pressurized arteries flows backward from the aorta through the aortic valve into the heart. This is because the leaflets are not in closed position leaving an open orifice in the aortic valve. Failure of the leaflets or cusps to close can be due to anatomic disruption of the leaflets or due to dilation of the aortic annulus.

It is an object of the present invention to prevent or reduce regurgitation of blood by improving the coaptation of the aortic valve leaflets during diastole without causing significant restriction during the systole, in other words restricting the inward flow of blood to the left ventricle by stenting or supporting the aortic valve without impeding outflow.

SUMMARY OF THE INVENTION

The invention resides in an aortic valve supporting device which comprises an annular portion located around a central axis. A plurality of stenting arms are cantilevered on the annular portion and extend axially from the annular portion. There is a hiatus formed in the annular portion to permit it and the stenting arms to be positioned by a surgeon around the aorta above the coronary ostia with the stenting arms located around the aortic annulus to apply a supporting force to the leaflets of the aortic valve. Were it not for the hiatus in the annular portion, the surgeon would have to sever the aorta, place one end through the annular portion, join the ends, and then suture the severed portion.

The device is made of a biocompatible plastic such as stainless steel or lexan acrylic plastic. The annular portion may be covered with fabric such as a cloth ring of biocompatible material to facilitate its being sutured in place. Collagen may also be employed.

In one embodiment of the invention, the stenting arms, which are cantilevered axially from the annular portion, have free ends which are formed closer to the central axis than the annular portion itself such that the arms without any external force applying member may apply a supporting force to the aortic valve when the device is in place.

There are means provided near the free ends of the cantilevered stenting arms to receive a force applying member to squeeze the stenting arms inwardly or in a direction toward the central axis.

Force applying means such as a cable tie or a simple knotted strand of suture material or the like may be employed to bias the stenting arms inwardly toward the central axis.

In accordance with another embodiment of the invention, the annular member is in the form of a flange extending away from the axis. The flange may be surrounded by a rotatable cap. The cap also has a hiatus to align with the hiatus in the annular portion or flange when the device is being placed in position around the aorta. In this embodiment, rotation of the cap will move its hiatus out of alignment with that of the annular member or flange to completely close the annular member. Either or both of the flange or the cap may include apertures to facilitate suturing of the device in place.

The above and other features of the invention including various and novel details of construction and combination of parts will now be more particularly described with reference to the accompanying drawings and pointed out in the claims. It will be understood that the particular aortic valve supporting device embodying the invention is shown by way of illustration only and not as a limitation of the invention. The principles and features of this invention may be employed in varied and numerous embodiments without departing from the scope of the invention.

DETAILED DESCRIPTION OF THE INVENTION

Figure 1:
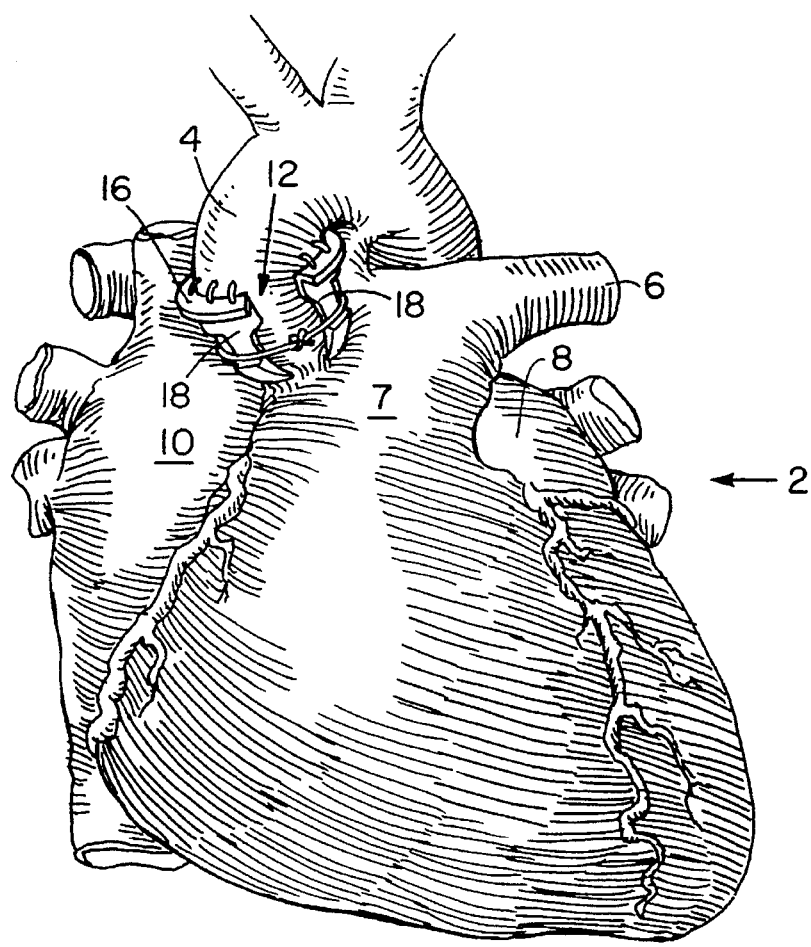
FIG. 1 is a perspective view of a heart with an aortic valve supporting device made in accordance with the invention sutured in place.

In FIG. 1, there will be seen a perspective view of a heart generally designated 2, the aorta is designated 4, the pulmonary artery 6, the area of the left ventricle 7, the area of the left auricle 8, and the area of the right auricle 10.

One embodiment of an aortic valve supporting device 12 is shown sutured in place around the aorta 4 above the coronary ostia. It includes an annular portion 16 and a plurality of stenting arms 18 cantilevered from the annular portion with their lower ends around the outside of the aortic annulus. Various embodiments of the supporting device will be described in greater detail hereinafter.

Figures 2, 3:
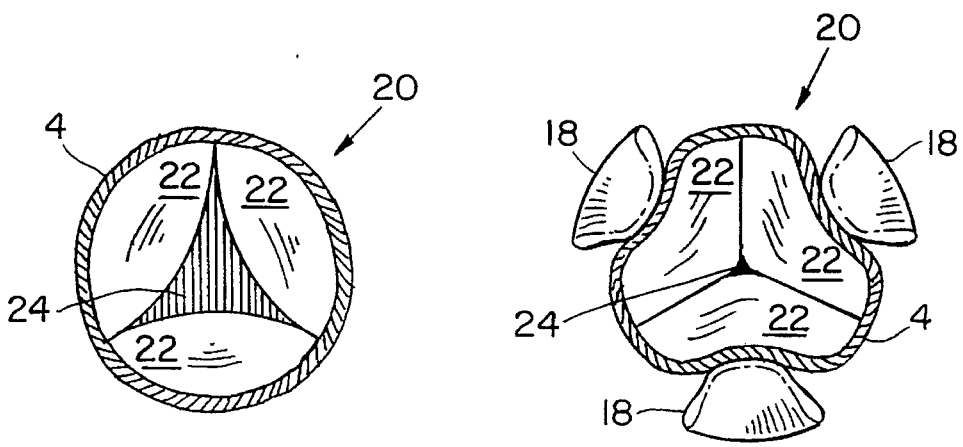
FIG. 2 is a section of a malfunctioning aortic valve showing its three leaflets or cusps not fully closed.
FIG. 3 is a view similar to FIG. 2 wherein the leaflets are shown in substantially closed position when the supporting device is in place.
Figure 6:
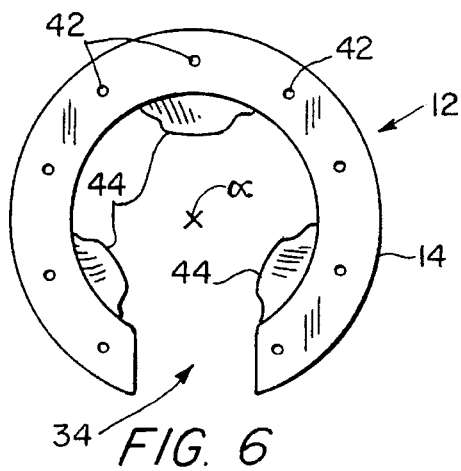
FIG. 6 is a plan view of the embodiment shown in FIG. 5.

Referring next to FIGS. 2 and 3, there will be seen sectional views through a malfunctioning aortic valve generally designated 20. The valve includes three leaflets or cusps 20 defining between them the aortic annulus or orifice 24. FIG. 2 shows the leaflets 22 not in closed position leaving a rather large orifice 24 open to regurgitation during diastole.

FIG. 3 shows the aortic valve 20 being stented or supported by the stenting arms 18 of the supporting device 12 and biased into closed position. It will be understood that the orifice or annulus 24 may not necessarily be stented into fully closed position but a small orifice may exist even after the valve supporting device has been sutured into position. Any reduction in the size of the orifice 24 is beneficial in reducing regurgitation.

Figure 4:
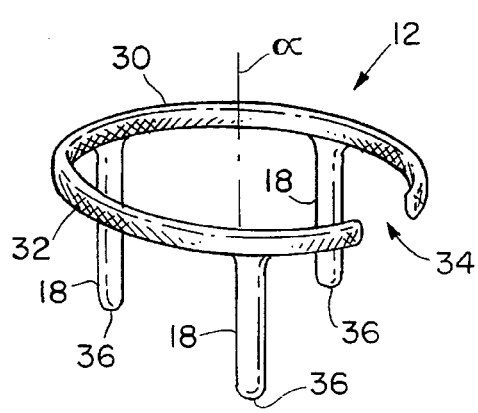
FIG. 4 is a perspective view of one embodiment of the present invention.

Referring next to FIG. 4, there will be seen one embodiment of the aortic valve supporting device 12. It includes an annular portion 30 located around a central axis α. A plurality of stenting arms, and in this case three, to correspond with the three leaflets of the aortic valve are cantilevered from the annular portion and extend axially of the central axis α. There may be more than three stenting arms but three has been found satisfactory since they correspond to the number of leaflets in the aortic valve.

The annular portion 30 of the supporting device may include a fabric covering 32 such as a biocompatible cloth ring to facilitate suturing. The device itself is made from a biocompatible material such as lexan or stainless steel.

Figure 8:
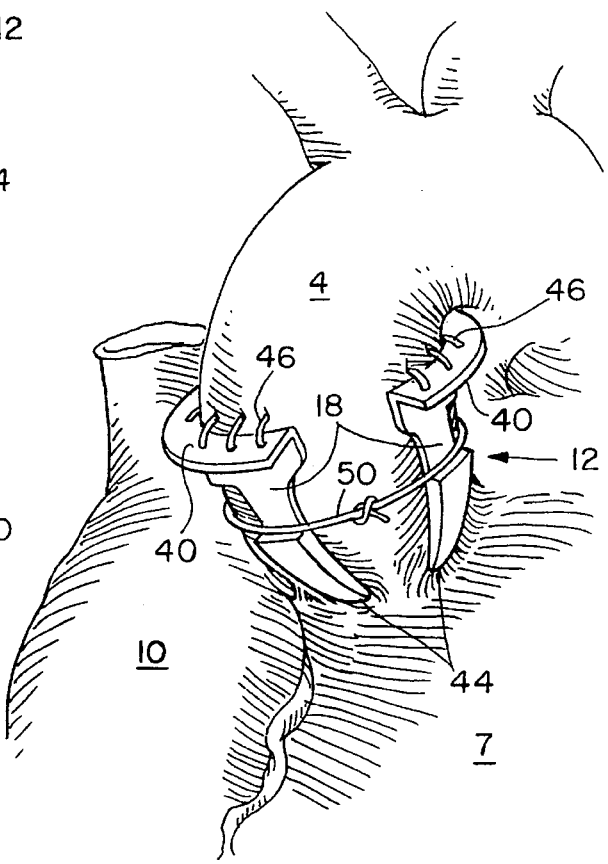
FIG. 8 is a perspective view on enlarged scale of the device shown in FIG. 5 sutured in position around the aorta.
Figure 7:
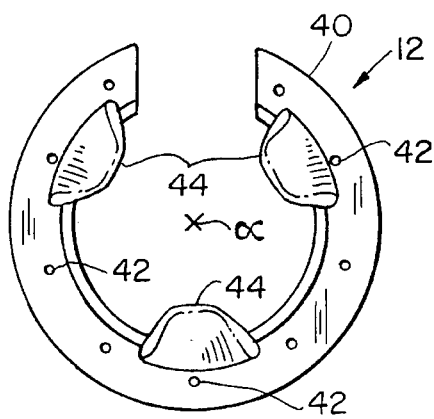
FIG. 7 is a bottom view of the embodiment shown in FIG. 5.

A hiatus is formed in the annular portion to permit the annular portion 12 and the stenting arms 18 to be positioned around the aorta as seen in FIGS. 1 and 8 with a minimum of surgery, the aorta being slid through the hiatus 34 prior to the device being sutured to the aorta.

The annular portion 30 is positioned downstream from the left ventricle above the coronary ostia such that the free ends 36 of the stenting arms will engage the outside of the aorta at the location of the aortic annulus such that the stenting arms apply a supporting force to the aortic leaflets or cusps to urge them inwardly as seen in FIG. 3 and reduce the size and close the annulus 24.

It will be understood that with the supporting device sutured into position, the supporting or stenting force is at all times applied to the valve but during systole, i.e. when the heart is contracting, the increasing left ventricular pressure causes the leaflets or cusps 22 to open to permit the normal outflow of blood. Then in diastole, when the heart is relaxed, the pressure of the stenting arms causes the leaflets or cusps to return to the FIG. 3 position preventing or substantially reducing regurgitation.

Figure 5:
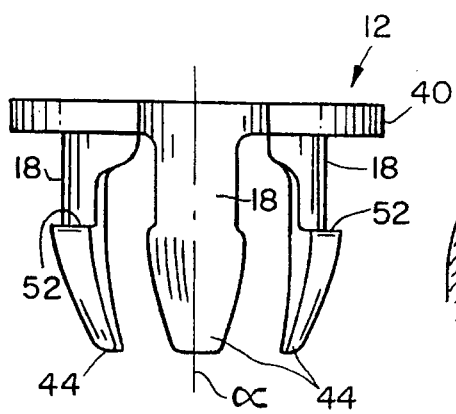
FIG. 5 is a front view of another embodiment of the invention.

Referring next to FIG. 5, another embodiment of the aortic valve supporting device 12 will be seen. The annular portion includes an annular flange 40 extending outwardly away from the central axis α. It too includes a hiatus 34 and the flange may be provided with a plurality of apertures 42 to facilitate suturing. As seen in FIG. 5, the stenting arms 18 curve inwardly and have free ends 44 positioned closer to the central axis α than the annular portion or flange 40. In the FIG. 5 embodiment when sutured in place as seen in FIG. 8 by sutures 46, the free ends 44 or the stenting arms 18, being closer to the central axis α, are in position to apply a stenting or supporting force to the aortic valve without additional force being applied to them.

Optionally, force applying means may be applied to the stenting arms 18 to further urge them inwardly toward the central axis α and into the stenting or supporting position.

The force applying means may be a simple knotted strand of suture material 50 or any convenient equivalent such as a cable tie such as the toothed plastic ribbons used to secure individual strands of electrical wires into bundles or cables. The stenting arms 18 may also be provided with retaining means 52 in the form of a lip or shelf to detain the force applying means 50 in position.

Figure 9:
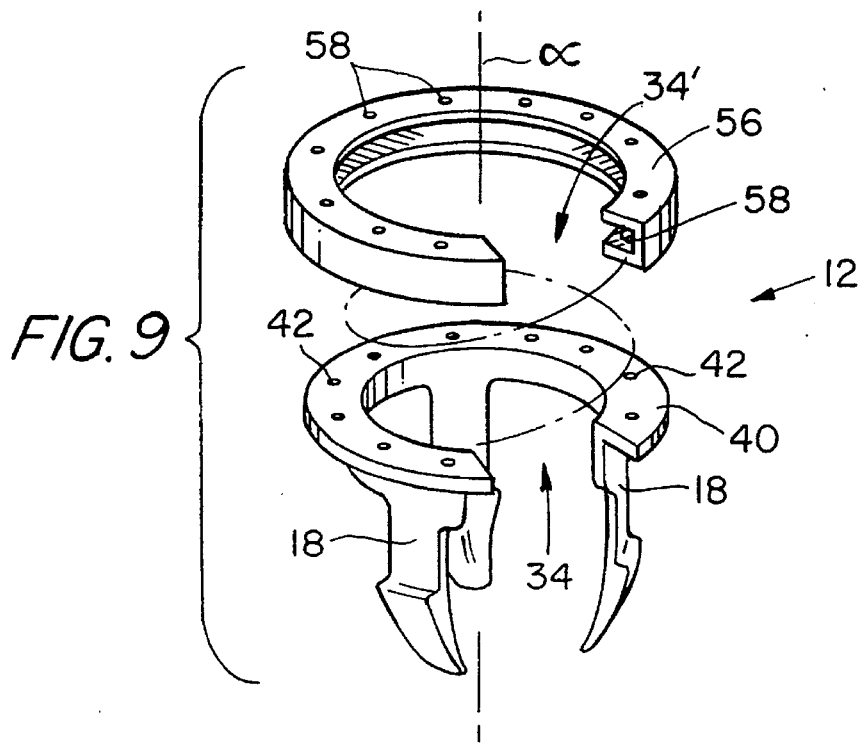
FIG. 9 is an exploded perspective view of another embodiment of the invention.
Figure 10:
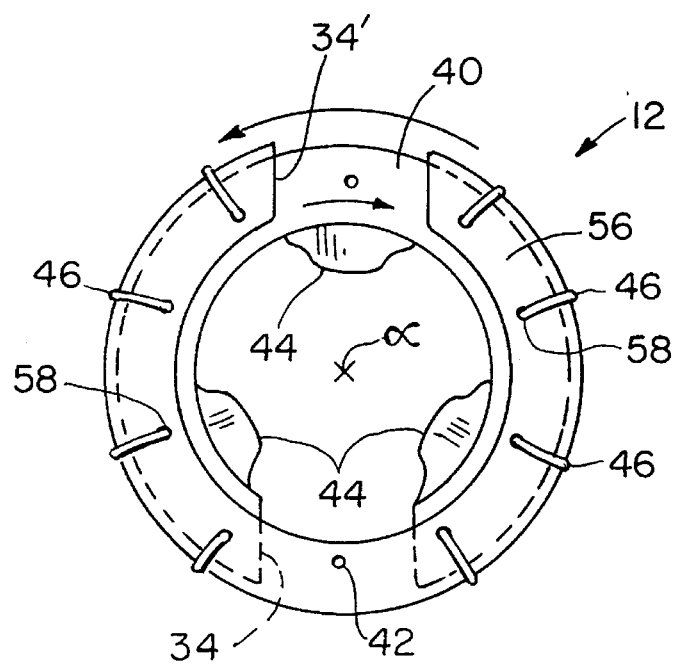
FIG. 10 is a top plan view of the embodiment shown in FIG. 9.

Yet another embodiment of the invention will be seen in FIGS. 9 and 10. An annular cap 56 having an internal groove 58, which is slightly larger than the diameter of the flange 40, is positioned over and surrounds the flange 40. The annular rotatable cap 56 also has a hiatus 34' of the same size as the hiatus 34 in the annular portion or flange 40.

When assembled, the surgeon aligns both hiatuses and slides the device over the aorta as seen in FIGS. 1 and 8 in the manner described above. The rotatable cap is also provided with apertures 58 corresponding to the apertures 42 in the flange 40 to facilitate suturing. Upon assembling the device, the rotatable cap 56 is rotated relative to the flange 40 to offset the hiatus 34' in the cap from the hiatus 34 in the flange, thus the annular member completely encircles the aorta. The surgeon will then align the apertures 58 with the apertures 42 in the flange 40 and suture the device through the aligned apertures to the aorta by sutures 46.

We claim:

1. An aortic valve supporting device comprising:

an annular portion located around a central axis, a plurality of stenting arms extending axially from the annular portion, a hiatus formed in the annular portion to permit the annular portion and the stenting arms to be positioned around an aorta with the stenting arms located to apply a supporting force to the aortic valve, and a rotatable member on the annular portion for closing the hiatus after the supporting device has been positioned around the aorta.

2. A device according to claim 1 wherein the device is made of a biocompatible plastic.

3. A device according to claim 1 wherein the annular portion includes fabric to facilitate suturing.

4. A device according to claim 1 wherein the member for closing the hiatus comprises a flange on the annular portion extending away from the axis and which flange is surrounded by a rotatable cap having a mating hiatus such that rotation of the cap will close the hiatus in the aortic valve.

5. A device according to claim 1 wherein the annular portion includes apertures to facilitate suturing.

6. An aortic valve supporting device comprising:

an annular portion located around a central axis, a plurality of stenting arms cantilevered axially from the annular portion, the free ends of the stenting arms being closer to the central axis than the annular portion, a hiatus formed in the annular portion to permit the annular portion to be positioned around an aorta with the free ends of the cantilevered arms located to apply a supporting force to the aortic valve, and a rotatable member on the annular portion for closing the hiatus after the supporting device has been positioned around the aorta.

7. A device according to claim 6 wherein the device is made of a biocompatible plastic.

8. A device according to claim 6 wherein the annular portion includes fabric to facilitate suturing.

9. A device according to claim 6 wherein the member for closing the hiatus comprises a flange on the annular portion extending away from the axis and which flange is surrounded by a rotatable cap having a mating hiatus such that rotation of the cap will close the hiatus in the aortic valve.

10. A device according to claim 6 wherein the annular portion includes apertures to facilitate suturing.

11. An aortic valve supporting device comprising:

an annular portion located around a central axis, a plurality of stenting arms cantilevered axially from the annular portion, a hiatus formed in the annular portion to permit the annular portion to be positioned around an aorta with the free ends of the cantilevered arms located to apply a supporting force to the aortic valve, a rotatable member on the annular portion for closing the hiatus after the supporting device has been positioned around the aorta, and force applying means engagable with the arms to bias them toward the central axis.

12. A device according to claim 11 wherein the device is made of a biocompatible plastic.

13. A device according to claim 11 wherein the force applying means is a cable tie.

14. A device according to claim 11 wherein the force applying means is a knotted strand.

15. A device according to claim 11 wherein there are retaining means on the arms to receive and position the force applying means.

16. A device according to claim 11 wherein the member for closing the hiatus comprises a flange on the annular portion extending away from the axis and which flange is surrounded by a rotatable cap having a mating hiatus such that rotation of the cap will close the hiatus in the aortic valve.

17. A device according to claim 16 wherein the flange includes apertures to facilitate suturing.

18. A device according to claim 16 wherein the flange and the cap include apertures to facilitate suturing.

19. A device according to claim 11 wherein the annular portion includes fabric to facilitate suturing.

* * * * *